United States Patent [19]

Koros et al.

[11] Patent Number: 5,273,519
[45] Date of Patent: Dec. 28, 1993

[54] BONGEUR SURGICAL INSTRUMENT

[76] Inventors: Tibor Koros; Gabriel Koros, both of 610 Flinn Ave., Moorpark, Calif. 93021

[21] Appl. No.: 781,559

[22] Filed: Oct. 22, 1991

Related U.S. Application Data

[63] Continuation-in-part of Ser. No. 608,659.

[51] Int. Cl.$^5$ .............................................. A61B 17/00
[52] U.S. Cl. ..................... 606/83; 606/170; 606/171; 606/185
[58] Field of Search ............... 606/79, 82, 83, 107, 606/170, 171, 175, 184, 185, 190

[56] References Cited

U.S. PATENT DOCUMENTS

| | | | |
|---|---|---|---|
| 3,752,161 | 8/1973 | Bent | 606/79 X |
| 3,835,860 | 9/1974 | Garretson | 606/79 |
| 4,476,863 | 10/1984 | Kanshin et al. | 606/171 X |
| 4,586,497 | 5/1986 | Dapra et al. | 606/79 X |
| 4,722,338 | 2/1988 | Wright et al. | 606/83 |
| 4,777,948 | 10/1988 | Wright | 606/171 X |
| 4,848,338 | 7/1989 | Desatnick et al. | 606/171 X |
| 5,061,269 | 10/1991 | Muller | 606/167 X |

OTHER PUBLICATIONS

"News Release", Zimmer Inc., Dated Oct. 1966.

Primary Examiner—Mickey Yu
Assistant Examiner—Sam Rimell
Attorney, Agent, or Firm—Jessup, Beecher & Slehofer

[57] ABSTRACT

The rongeur has a frame with a medial horizontal channel in one portion and a stationary handle at the other portion. A carriage is slidably engaged in the channel. A movable handle is attached at a fulcrum arm at the bottom front of the frame. A two-piece shaft extends from an integral cover & barrel secured to the carriage. The shaft has a stationary lower half, and an upper half that reciprocates on the stationary half to open and close the bite area at the tip of the shaft in response to the surgeon gripping the handles. The shaft halves are held together by a slidable joint. The cover & barrel with the extended shaft can be cocked open to remove the shaft. The tip of the shaft has a closable bite area and is used to remove tissue or to take a biopsy. The tip can be rotated to various angles after pressing a release lever. Also, the shaft can be quickly removed and replaced with another shaft having a different tip. During normal use, the tension spring maintains the carriage and attached cover & barrel, and shaft stationary in the channel. Excessive squeezing of the handles by the surgeon while the surgeon has the instrument in his grip causes the carriage, cover & barrel and extended shaft to move to compensate for the excessive squeezing by the surgeon. The tension spring flexes to allow the carriage to move slightly. It provides a safety cushion, and prevents the tip from being damaged.

9 Claims, 9 Drawing Sheets

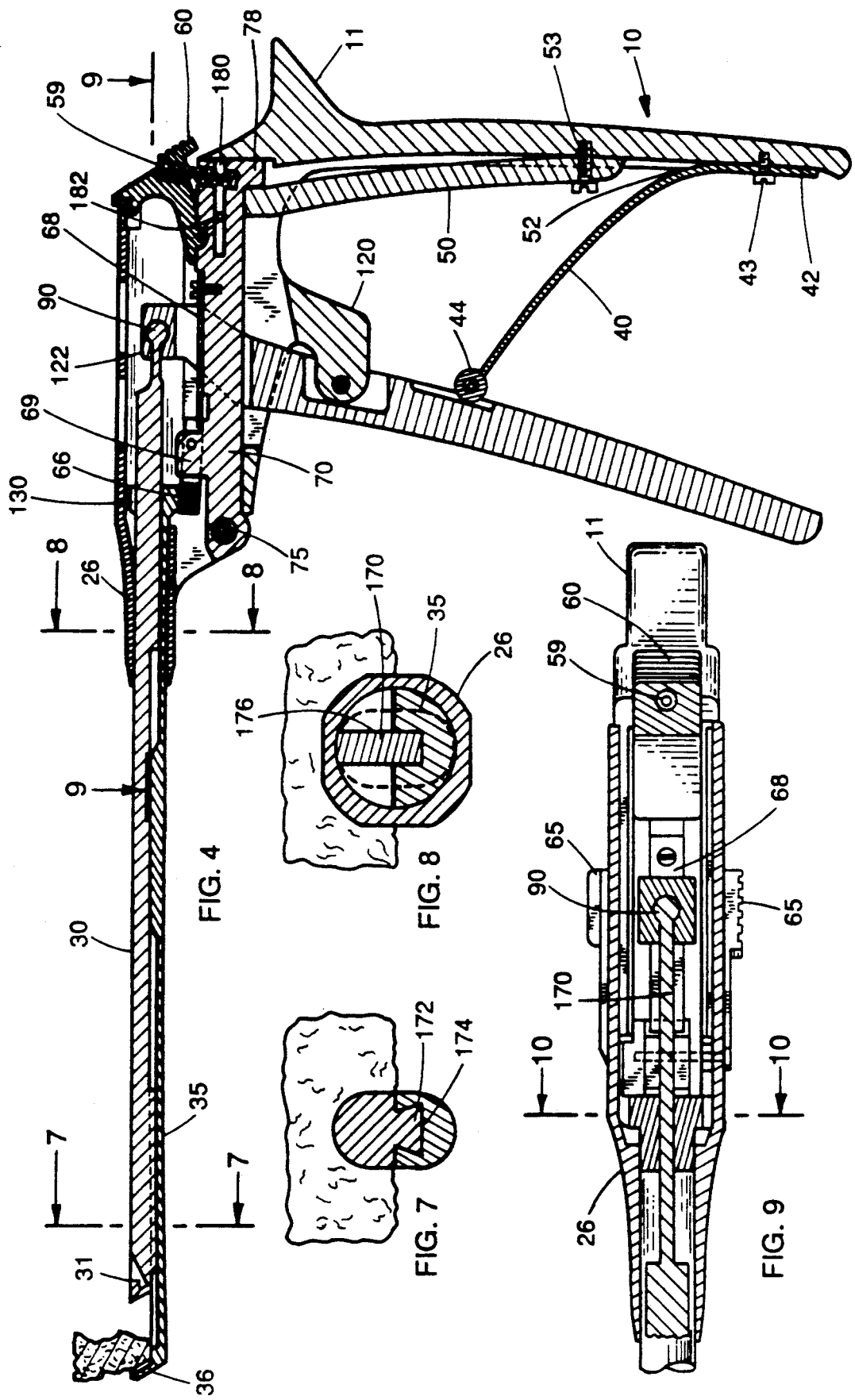

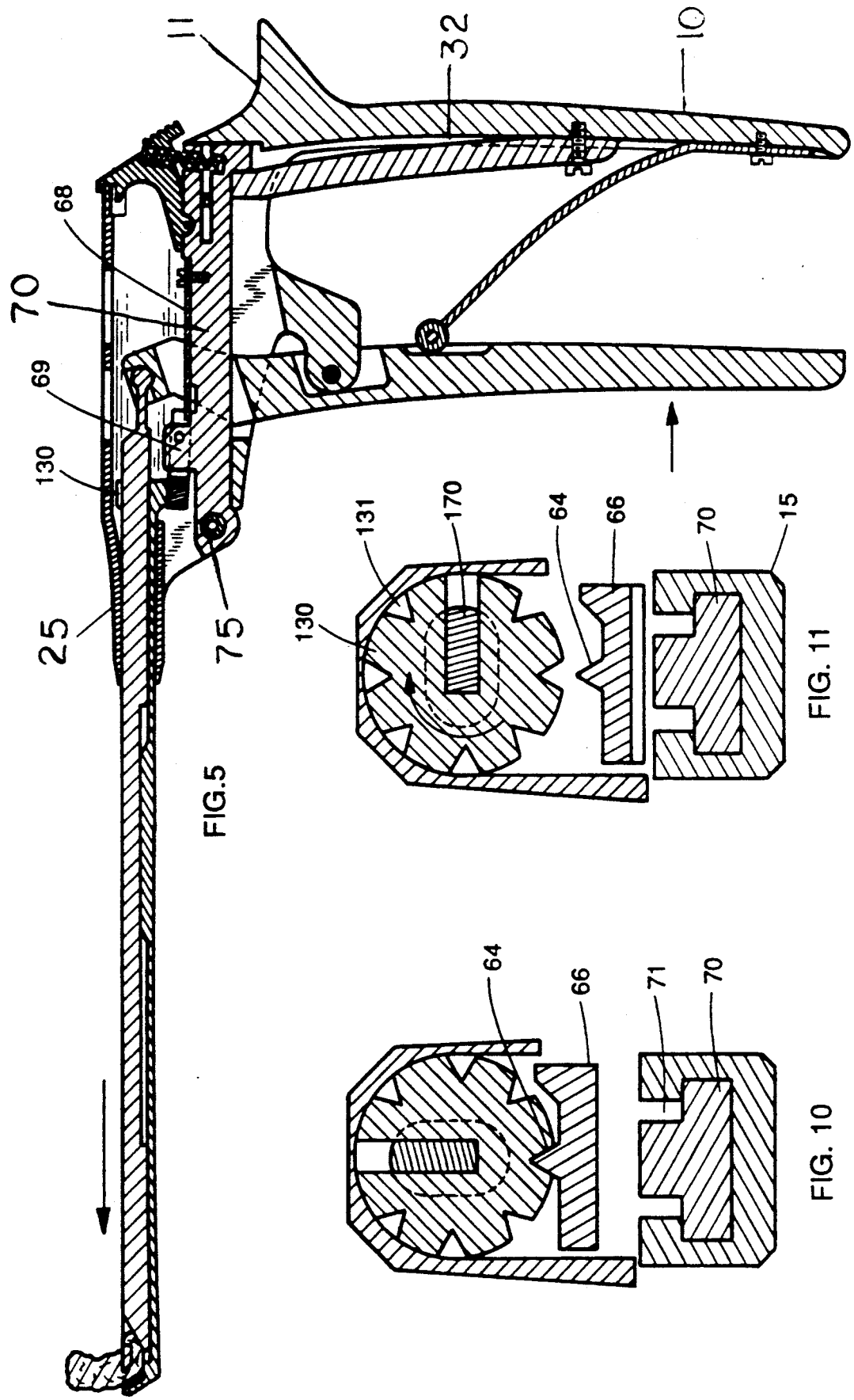

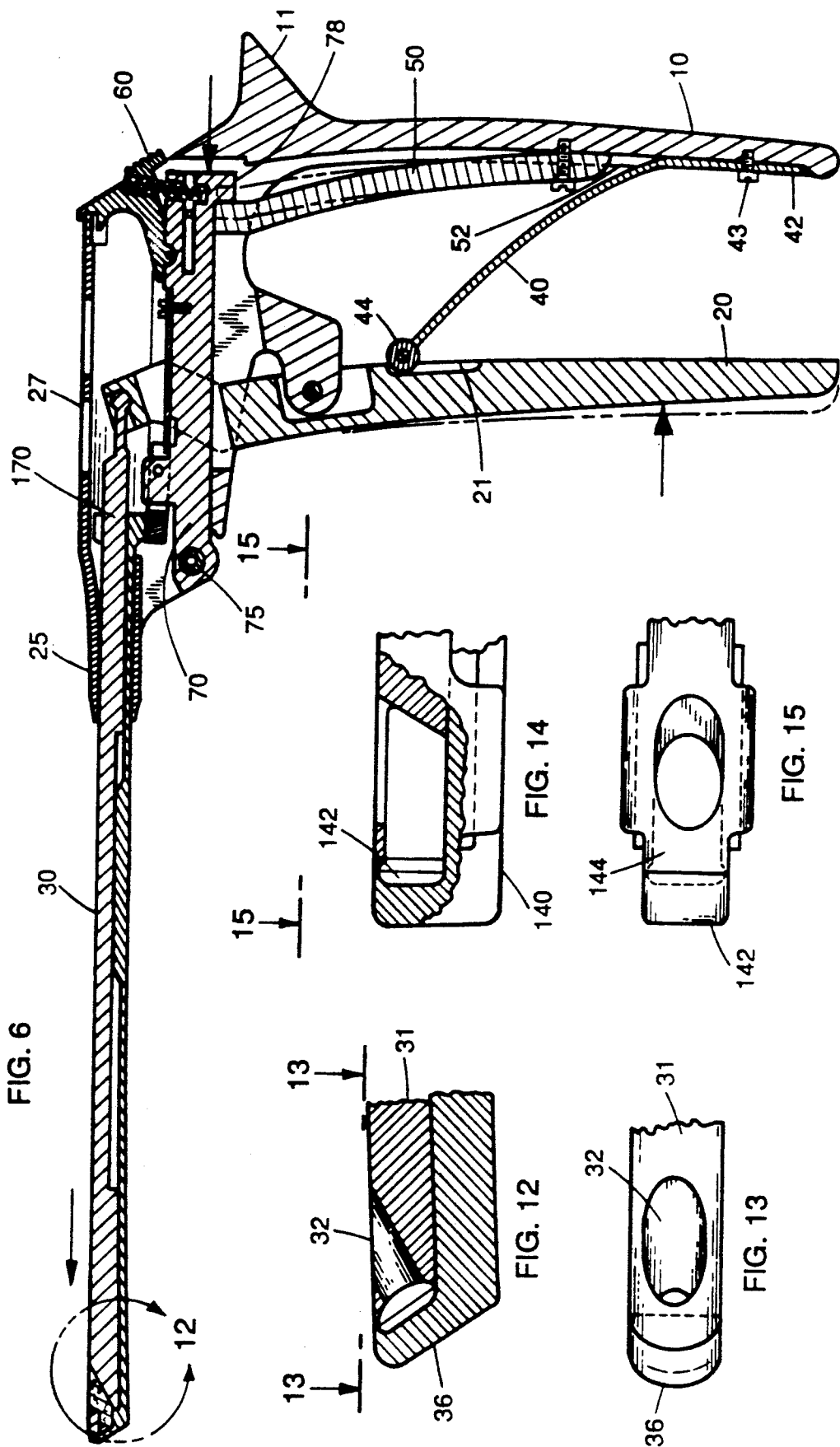

BONGEUR SURGICAL INSTRUMENT

CROSS REFERENCE TO RELATED APPLICATIONS

This is a continuation-in-part of utility patent application Ser. No. 07/608,659 filed on Nov. 2, 1990, which is now abandoned.

BACKGROUND OF THE INVENTION

1. Field of the Invention

Medical and laboratory equipment: fixed apparatus for equipment; instrument or tool for medical or laboratory use; surgical forceps. Surgery: surgical instruments; orthopedic cutting instrument; rongeur resector or nipper; gouge forceps, and instrument for removing tiny fragments of bone; forceps having jaws biased to open or closed position. Forceps having a jaw structure; forceps having a hinge or latch structure; forceps having a tubular member stripper.

2. Description of the Prior Art

FIG. 1 of the drawings illustrates a typical prior art rongeur. The rongeur is a hand held device used by a surgeon while performing surgery. The illustrated rongeur is commonly referred to as a laminectomy bone rongeur. There is also available a Kerrsion pituitary rongeur, which has a scoop-like cutting head such as the one illustrated in FIGS. 16–18 in the drawings. There are perhaps fifty different styles of rongeurs available. The different versions are a result of different cutting tips, different rongeur lengths usually being from six inches to eleven inches, and different handle grips and spring combinations. The proximal tip of the rongeur is its essence. The surgeon requires a surgical instrument that can be used to remove calcification, to trim away part of a bone, and to assist in bone fusions. The rongeur is also commonly used to take tissue samples for biopsy purposes, and to remove portions of tissue during the operation.

The typical prior art rongeur has an angled upright rear stationary handle which changes at its upper portion into an integral stationary shaft extending horizontally from the upper portion of the stationary handle. The distal end of the stationary shaft has an immovable cutting tip. There is a second upright movable handle attached near its upper end by a pin screw to the area where the stationary handle changes to the stationary shaft. The attachment functions as a fulcrum point for the movable handle. The pair of handles form an inverted V-shape in profile. There is a movable shaft which rests on top of the stationary shaft. The distal end of the movable shaft also has a cutting tip and its proximal end engages with the top of the movable handle. The pair of shafts have complementary tongue and grooves to keep them slideably locked together. The tongue and groove joint also allows the movable shaft to slide back and forth over the stationary shaft. An inverted V-shaped tension spring is placed between the two handles to keep them spread open sufficiently and also to keep the two cutting tips open at the tips of the shafts. The spring also provides resistance and gives tactile feel to the surgeon when he is squeezing or relaxing his grip on the handles while using the rongeur. By squeezing the handles together, The top end of the movable handle pushes against the proximal end of the movable shaft. As a result, the moving cutting tip on the movable shaft slides toward the stationary cutting tip on the stationary shaft. The open bite area between the two tips is positioned at the place where the surgeon wishes to remove material. Any material positioned in the bite area while the surgeon squeezes the handles together will be snipped off or punched out as a result of the movable cutting tip pressing against the stationary cutting tip.

The stationary cutting tip can have many configurations. It is typically pointed up or down and frequently has an offset angle. The perimeter of the tip extending from the shaft forms a semicircle in profile from 3 to 5 millimeters in diameter. This area inside the perimeter usually has a recessed cavity to allow for the snipped off piece of bone or tissue to lodge itself. The movable cutting tip has a bevelled edge with a flat or recessed face. The two tips form complementary faces and edges so that there will be a clean cut made by the rongeur.

A series of rongeurs having different tips and sizes are made available for the surgeon during the operation so that he or she can use them as called for. The tip style for a particular rongeur cannot be changed, nor can the typical rongeur be disassembled after use for ease in cleaning or for replacement of broken parts.

The most serious shortcoming found in the typical rongeur is in the frequency of broken tips. A broken tip renders the rongeur useless. It cannot be refurbished economically and is usually discarded. It is an important object for nearly all rongeurs to have a small cutting tip, which is commonly referred to as a small footplate. Surgeons request the small tips because they are easier to work with and they minimize the trauma caused by the surgery itself. A typical rongeur is designed to withstand 500 pounds of force or stress at the tip before breaking. When the surgeon grips and squeezes the handles towards each other, the squeezing force is multiplied by the lever action of the movable arm pushing against the proximal end of the movable shaft. The movable cutting tip is caused to press against the stationary tip in response to the surgeon's squeezing grip. The stationary tip has to be able to withstand the force of the movable tip pressing against it during the snipping and cutting process. If the force exerted by the surgeon exceeds the designed limits, the stationary tip or shaft will bend or break. The surgeon's requirement for a small footplate places limits on the structural strength and rigidity of the stationary shaft. As a result, breakage is common from over squeezing by the surgeon. Because of this shortcoming, replacement of expensive rongeurs and maintaining an inventory of different tipped rongeurs results in unnecessary expenses for hospitals, which is passed along to the patient.

The inventor realized this problem and invented the rongeur as shown and described herein to alleviate or solve the aforementioned problems regarding prior art rongeurs.

SUMMARY AND OPERATION OF THE INVENTION

The present invention has a frame with a medial horizontal channel in one portion and a stationary handle at the other portion. A carriage is slidably engaged in the channel. A movable handle is attached at a fulcrum arm at the bottom front of the frame. A two-piece shaft extends from an integral cover & barrel secured to the carriage. The shaft has a stationary lower half, and an upper half that reciprocates on the stationary half to open and close the bite area at the tip of the shaft in response to the surgeon gripping the handles. The shaft halves are held together by a slidable joint. The cover & barrel with the extended shaft can be cocked open to remove the shaft. The tip of the shaft has a closable bite area and is used to remove tissue or to take a biopsy. The tip can be rotated to various angles after pressing a release lever. Also, the shaft can be quickly removed and replaced with another shaft having a different tip. During normal use, the tension spring maintains the carriage and attached cover & barrel, and shaft stationary in the channel. Excessive squeezing of the handles by the surgeon while the surgeon has the instrument in his grip causes the carriage, cover & barrel and extended shaft to move to compensate for the excessive squeezing by the surgeon. The tension spring flexes to allow the carriage to move slightly. It provides a safety cushion, and prevents the tip end of the shaft from being damaged.

Expressed another way, the present invention is generally referred to as a rongeur, which is a forceps type of surgical instrument for removing calcifications, to trim away a portion of bone, or to remove parts of tissues for biopsy purposes. The present invention includes a frame, a carriage mounted in a medial horizontal slotted channel in the frame, a stationary handle formed as part of and at the rear of the frame, a lever action movable handle attached to an arm extending from the bottom midsection of the frame, a combination barrel and chamber cover, and a two-piece shaft having a cutting tip. The barrel portion is hingedly secured to the front portion of the carriage. The barrel and cover chamber combination can be cocked open and the two-piece shaft can be quickly removed from and reinserted into the barrel. Different types of two piece shafts are interchangeable with the barrel of the same rongeur.

The two-piece shaft is further defined as having a stationary shaft, a movable shaft, a movable cutting tip and a stationary cutting tip at the distal end, and a star gear or wheel at the proximal end. The distal end where the cutting tips of the movable and stationary shaft form a slight gap is referred to as the jaws or bite area of the instrument. The distal end of the combination shaft where the tips are located is known in the surgical industry as the footplate.

It is always an objective of a rongeur manufacturer to provide for a small footplate in its rongeurs. The surgeon demands a small footplate, because it makes the rongeur easier to work with and a small footplate can remove smaller bits of bone and tissue. The major drawback of a small footplate is that as the cutting tip of the movable shaft and the tip of the stationary shaft come together to nip off a piece of bone, the pressure exerted by the surgeon while gripping the rongeur's handles will occasionally cause the footplate area to permanently deform or break resulting in a broken rongeur instrument, which cannot be used again and has to be discarded. A small footplate results in compromising the strength and integrity of the tip, because of metallurgical limitations. A small footplate requires the manufacturer to use less metal to keep everything to small dimensions.

The present invention includes a tension limiting element which automatically compensates for any excessive squeezing together of the handles by the surgeon. By automatically compensating for and correcting for any excessive squeezing by the surgeon, the integrity of the footplate is maintained, and it will not deform or break. The minor tension compensating element includes a flexible tension spring angularly positioned between the stationary handle and the movable handle to partially resist the squeezing force applied by the surgeon's grip. The tensioning spring also functions to separate the tips of the movable and stationary shafts when the surgeon relaxes his grip. This then allows the surgeon to dislodge the material from the tip of the rongeur after the cut has been made. The major tension compensating element is a vertically positioned stiff spring, which is screwed to the inside edge of the stationary handle. The stiff spring maintains the carriage in place and stationary on the frame. The carriage has the capability to move slightly, or to slide back and forth in its medial and horizontally positioned grooved channel in the frame. The reciprocal sliding action is very limited, and is used to compensate for the surgeon compressing the movable handle too closely towards the rigid stationary handle. The carriage can slide back and forth within a very limited range. The top edge of the stiff spring presses against a transverse ledge extending downwardly from the underside of the carriage. The ledge is also located towards the back of the carriage. The stiff spring biases the carriage with the attached cover, barrel and shafts against the stationary handle. The proximal end of the stationary shaft has a ball mounted to it. When sufficient force is applied to the stationary tip by the movable tip pressing against it, which is caused by the top of the movable handle pressing against the ball end of the movable shaft, the stiff tension spring will give and flex slightly to allow the carriage, cover & barrel, and shafts to move relative to the rigid frame and integral stationary handle. As a result, there can be only so much force applied at the footplate by the surgeon regardless of how hard he grips and squeezes the handles to cut the bit of bone.

There are additional novel features incorporated in this invention. The cover and barrel can be cocked open to provide access to the shafts. This feature allows for the use of different types of footplates to be used, because the invention has provision for interchangeable pairs of shafts. The pair of stationary and movable shafts can be pushed back out of the open barrel and can be replaced quickly with another new or different pair of shafts having a different footplate. Disposable biopsy shafts can be easily loaded in the open barrel.

Yet another feature found in this invention is the combination shaft, which can be rotated at 45 degree increments about its axis to change the footplate orientation relative to the barrel to allow greater versatility of use of the instrument by the surgeon. This feature affords the surgeon a variety of angles in one versatile instrument. It also complements the surgeon's technique. To accomplish this, there is a star gear or wheel secured towards the proximal end of the stationary shaft. There is a locking member, which prevents the star gear and therefore the combination shaft from rotating once the barrel and chamber cover part is closed. The surgeon simply depresses either quick release lever, rotates the combination tip to the desired angle, and then releases the lever to relock the shafts and tips at their new radial angle. There are a pair of quick release levers mounted on either side of the frame to make the instrument ambidextrous.

In an alternate, the star gear is replaced with a frustoconical section. The round proximal head is beveled radially around its circumference. The looking member has a wedge-shaped tooth that frictionally engages against a portion of the beveled edge and acts as a brake to prevent the combination shaft from rotating while in use. There is also a cylindrical threaded hollow bushing screwed in the bore of the barrel. The hollow bore of the bushing is funnel-shaped for receiving and holding the proximal end of the combination shaft. The surface of the frusto-conical section of the stationary shaft fits securely in the funnel portion of the bushing bore. The two surfaces also assist in preventing the combination shaft from rotating, and the bushing aligns and securely holds the combination shaft in place while the instrument is in use.

The proximal end of the movable shaft has a ball-shaped projection which fits into a socket type of recess in the top of the movable handle. The movable shaft slides along the flat top surface of the stationary shaft in response to the surgeon squeezing and moving the movable handle toward the stationary handle. The frame has an fulcrum arm extending from below its midsection where the movable handle is attached to it. This is the fulcrum point for the movable handle, which allows it to move about this point. The distance from the bottom of the handle to the fulcrum point is about twice the length of the distance from the fulcrum point to the socket recess at the top of the handle. The lever action resulting from force being applied against the handle by compressing the handle towards the other handle results in much greater force applied against the ball end of the movable shaft. This multiplied force is transferred to the movable cutting tip causing it to bear down hard against the stationary tip or a bone positioned in the bite area of the tip.

Each of the two shaft portions near the proximal end of the barrel form a hemicylinder. There is a longitudinal medial rectangular channel or keyway formed in the top flat surface of the hemicylinder of the stationary shaft. The movable shaft adjacent this portion is rectangular-shaped in cross section and it slides back and forth along the short edge in the rectangular channel cut in the flat top surface of the stationary shaft. The short edge can be referred to as a key that slides back and forth in the keyway. The interrelationship between the movable shaft and the stationary shaft changes towards the cutting tips end to form a dovetail joint where the stationary shaft has the inverted V-shaped groove while the movable shaft has the complementary V-shaped tongue. This dovetail sliding joint prevents the tip of the movable shaft from separating from the stationary shaft. It also keeps the tips in alignment. The combination shaft with the frusto-conical proximal end has the slip joint modified to a T-shaped tongue extending upwardly from the stationary shaft, and the complementary T-shaped groove in the movable shaft.

The present invention includes a locking trigger mounted towards the back of the instrument. The trigger is spring loaded so that the barrel and chamber cover combination is kept in the locked position and will not open unless the trigger is depressed. The previously discussed pair of quick release levers mounted on the left and right sides of the frame can be depressed to allow the combination shaft to be rotated in the barrel to change angular orientation to the combination cutting tip. There is a flat spring secured to the top of the movable carriage that keeps pressure on the locking means. The locking means is pivotally secured to the carriage so that the star gear or frusto-conical section can not rotate unless the quick release lever is depressed.

BRIEF DESCRIPTION OF THE DRAWINGS

FIG. 4 is a full longitudinal sectional view taken along the line 4—4 of FIG. 3 showing the jaws or cutting tips in the fully open position and the movable and stationary handles in the fully open at-rest position before a piece of the bone is excised. FIG. 4 is the first stage in the bone excision process.

FIG. 5 is a sectional view of the invention similar to FIG. 4 showing the cutting tips in the intermediate position and in the process of excising a piece of bone. The movable handle is in the intermediate closing mode. FIG. 5 is the middle stage of the bone excision process.

FIG. 6 illustrates the final stage after FIGS. 4 & 5 in the bone excision process.

FIG. 7 is a transverse sectional view taken along the line 7—7 of FIG. 4 and illustrating the inverted V-shaped tongue and groove joint in the distal portion of the stationary and movable shafts. The distal portion of the combination shaft is oval-shaped in cross section.

FIG. 8 is a transverse sectional view taken along the line 8—8 of FIG. 4 illustrating the rectangular tongue and groove continuing joint, also referred to as a keyway and key. The combination shaft is circular in cross section at this place. The cross section of the barrel and circular bore are also illustrated.

FIG. 9 is a longitudinal section taken along the line 9—9 of FIG. 4 and illustrating the interior components of the present invention.

FIG. 10 is a transverse sectional view taken along the line 10—10 of FIG. 9 and illustrating the star gear or wheel on the stationary shaft.

FIG. 11 is a view similar to FIG. 10 and illustrates the two-piece shaft with its radial angular orientation changed 90 degrees clockwise from that shown in FIG. 10. This results in the radial angular orientation of the cutting tip also being changed the same number of degrees, or 90 degrees in this view.

FIG. 12 is a sectional fragmentary view of the circle 12 in FIG. 11 and illustrating the cutting tips at the ends of both the removable and stationary shafts.

FIG. 13 a partial top plan view of the preferred embodiment of the cutting tips taken along the line 13—13 in FIG. 12.

FIG. 14 is a sectional fragmentary view of an alternate embodiment of the tip of the stationary member.

FIG. 15 is a partial top plan view taken along the line 15—15 of of FIG. 14.

DETAILED DESCRIPTION OF THE INVENTION

Figure 1:
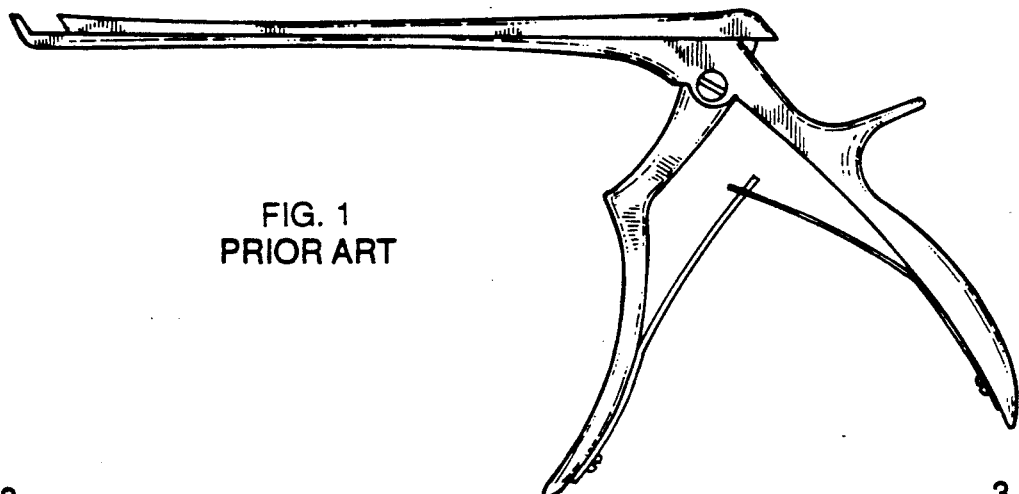
FIG. 1 is a left side elevational view of a typical prior art Rongeur bone punch. It is European made and is known as the Eberhardt device.
Figure 2:
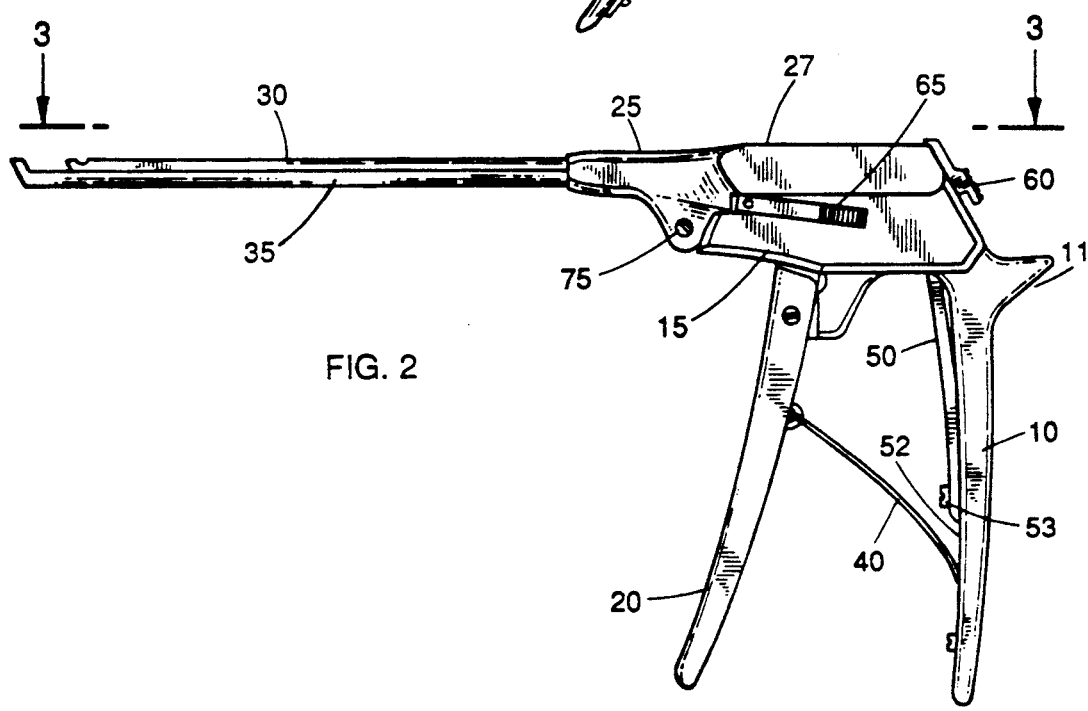
FIG. 2 is a left elevational view of the invention.
Figure 3:
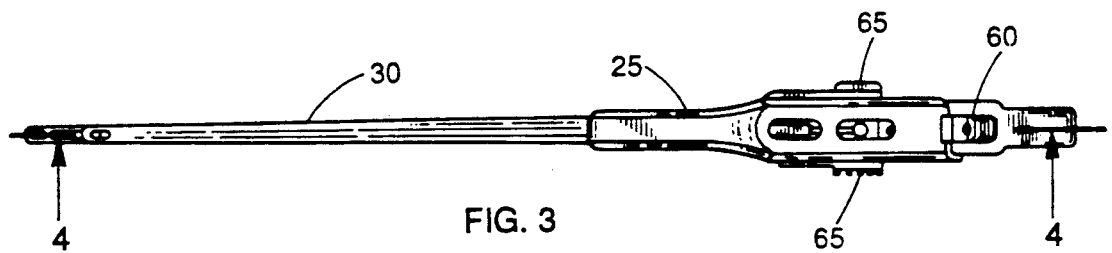
FIG. 3 is a top plan view of the invention taken along the line 3—3 of FIG. 2.

The invention will now be discussed in greater detail. Referring now to FIGS. 2 and 3: they illustrate the side elevational view and top view of the present invention when it is ready to be used. There is shown the stationary handle 10 integral with the frame 15; the movable handle 20; the openable and closeable barrel 25; the movable shaft 30 and stationary shaft 35 extending from the barrel 25; a flexible tension spring 40 to keep the movable handle 20 fully extended, a stiff spring tension limiting element 50 secured to the inside edge of the stationary handle 10; a trigger 60, a pair of quick-release levers 65 on either outside wall of the cover 27, and a movable carriage 70 (not shown in either FIG. 2 or 3) positioned in a slotted channel 71 in the frame 15.

The movable carriage 70 will now be discussed in greater detail along with the rigid frame 15 in which the movable carriage 70 is slideably secured. FIG. 6 and FIG. 10 illustrate the carriage 70 in great detail. The stationary handle 10 is vertically oriented with the thumb grip 11 extending horizontally as an extension from the frame. The stationary handle 10 and the frame is fabricated as a one-piece unit. The carriage 70 forms an inverted T-shape in cross section, as illustrated in FIG. 10 and slides back and forth in a cavity referred to as a horizontal inverted T-shaped channel 71 formed in the frame 15. The front end of the carriage 70 has a transverse hole with a pin 75 through it for hingedly securing the barrel 25 to the carriage 70. The barrel 25 can be cocked open by pivoting on this pin 75 secured to the end of the carriage 70. The other end of the carriage adjacent to the inside edge 52 of the stationary handle 10 has a transverse shoulder 78 extending downwardly. This shoulder 78 abuts against the upper inside edge of the stationary handle.

The stiff spring 50 is vertically positioned and has its bottom edge fastened to the inside edge 52 of the stationary handle with a screw 53. The top edge of the stiff spring 50 abuts against the shoulder 78 of the carriage. The stiff spring exerts counter pressure on the shoulder and thereby the carriage to keep the carriage pressed against the inside edge 52 of the stationary handle. As a result, the carriage is always stationary and at this location, unless excessive force is applied by the surgeon to the handles while using the invention. If the surgeon, while compressing the movable handle 20 towards the stationary handle 10, exceeds the threshold force at the cutting tips as determined by the stiffness of the stiff spring, then the carriage 70 will begin to slide away from the stationary handle, along with the barrel 25 and cover 27, and shafts 30 and 35. The stiff spring 50 is a safety feature, because if the top 122 of the handle 20, which pushes against the ball end 90 of the movable shaft 30 is forced hard enough against the ball 90, the tip 31 of the movable shaft 30 pressing against the tip 36 of the stationary shaft 35 will force both shafts, the barrel and cover, and carriage to move away from the stationary handle 10.

Figure 6A:
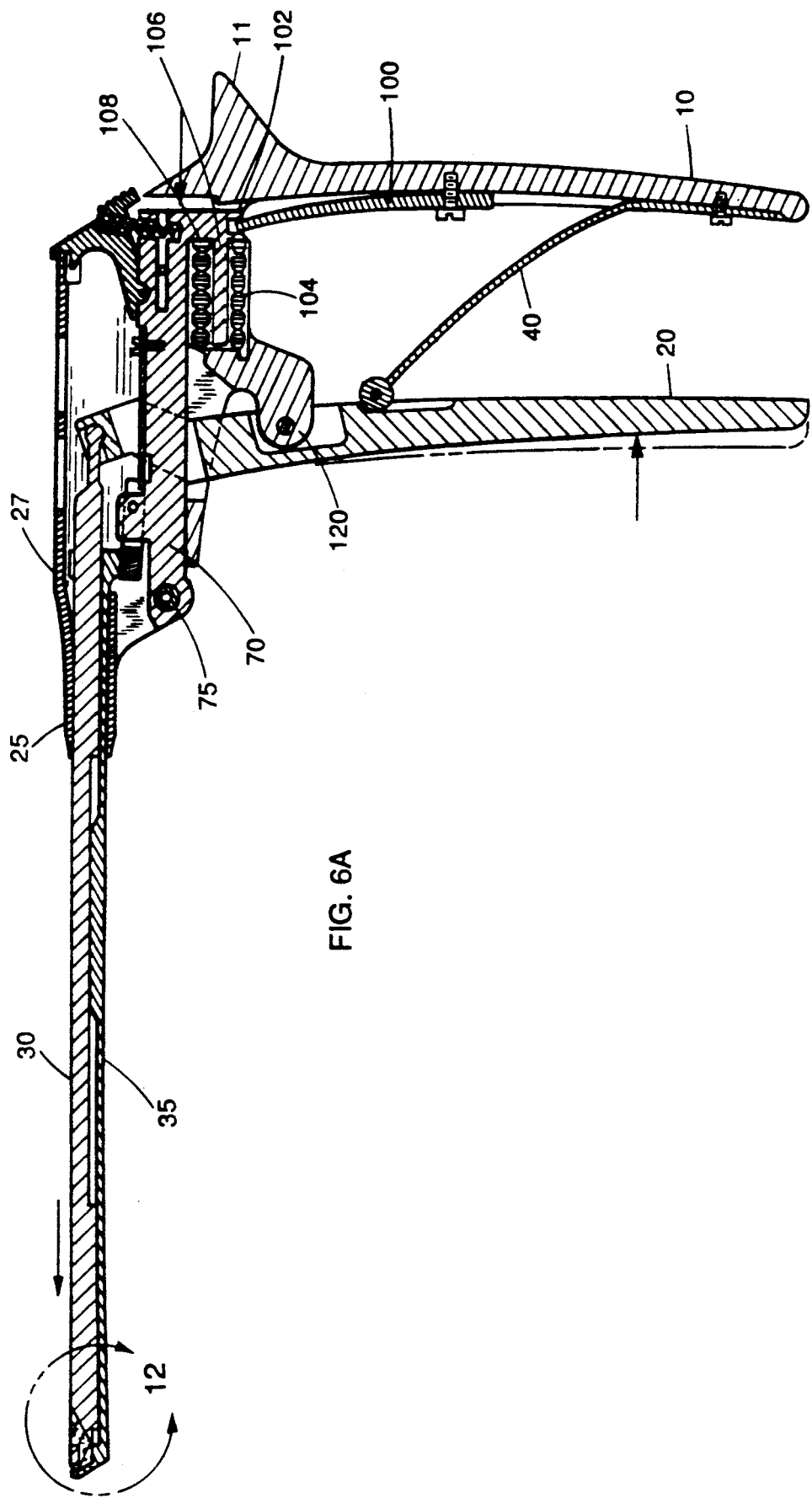
FIG. 6A is similar to FIG. 6 and illustrates a modified stiff tension limiting spring and an additional horizontal coil spring or belleville spring.

A modification of the stiff spring is illustrated in FIG. 6A. The shoulder 78 in the carriage is replaced with a transverse groove 102 into which the top edge of a modified stiff spring 100 is fitted. There is an additional horizontal cavity 104 in the frame for holding another spring 108 and a horizontal rod 106 extending from below the carriage 70. The spring 108 can be a conventional coil spring, or a series of belleville washers. The horizontal rod 106 is part of and extends from the bottom of the carriage. The rod centers and holds the compressible spring means so that the spring means will compress and act as a resistance to the carriage moving to the left in the frame. The area of the carriage where the rod is attached is the surface that pushes against the end of the spring means and compresses the spring means in the cavity as the carriage moves to the left in the frame. FIG. 6A illustrates the carriage at about the maximum movement to the left caused by the surgeon over squeezing while gripping the handles while using the rongeur during surgery. The stiff spring means 100 and the compressible spring 108 act together to resist movement of the carriage. Both springs allow for a more gradual threshold resistance to allow the carriage to move in response to excessive squeezing pressure.

In either alternate, there is another tension spring 40 which has one end 42 fastened by a screw 43 to the inside edge 52 of the stationary handle 10. The spring 40 has a roller 44 attached to the other free end, which is positioned in a small recess 21 on the inside edge of the movable handle 20. The purpose of this tensioning spring 40 is to keep the movable handle 20 at a predetermined distance from the stationary handle 10 when the invention is at the at-rest position resulting in the tips 31 and 36 of the shafts also being in the open, at-rest position. The shelf 131 on the stationary shaft limits how far the bite area can open. This is referred to as the bite of the instrument. Whenever the surgeon squeezes the handles, this other tensioning spring 40 also acts as a resistance to prevent the surgeon from bearing down too hard when he is removing a portion of bone or the like. The spring also provides a tactile feel to the instrument so that the handles spread apart when the surgeon relaxes his grip. It also opens up the bite to allow the tissue to be removed.

Figure 16:
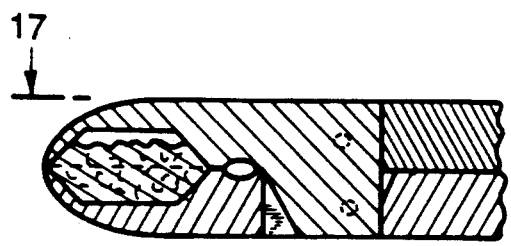
FIG. 16 is a fragmentary longitudinal sectional view of a second alternate illustrating a pivotal jaw scoop member attached to the tip of the movable shaft.
Figure 18:
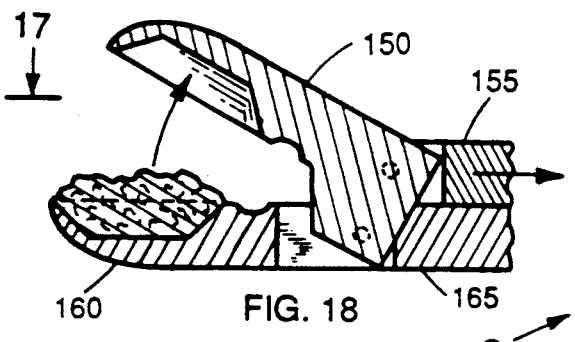
FIG. 18 is a sectional view similar to FIG. 16 illustrating the pivotal jaw scoop member in the open position.
Figure 17:
FIG. 17 is a fragmentary top plan taken along the line 17—17 in FIG. 16 and illustrating the tip of the pivotal jaw scoop member.

The upper portion of the movable handle 20 is pivotally secured to an arm 120 being integral with and extending below the frame in the midsection area. There is an opening in the bottom of the frame and a slot in the carriage to provide the movable handle access to the end of the movable shaft. The upper end of the movable handle 20 has a rounded recess or socket 122 which mates with the ball end 90 of the movable shaft 30. The ball-shaped head 90 at the proximal end of the movable shaft 20 joins with the rounded recess 122 at the top of the movable handle so that when the movable handle is squeezed and pivots forward about its fulcrum point at the mounting arm 120 extending below the frame, the rounded recess 122 will push against the ball 90 causing the movable shaft 30 to slide towards the tip 36 of the stationary shaft 35 to close the bite to remove a portion of bone or tissue for biopsy purposes. The movable shaft reciprocates or slides back and forth relative to the stationary shaft. The stationary shaft has a hemicylindrical shape at its proximal portion. The proximal end of the stationary shaft has a star gear or star wheel 130 secured to it while the distal end has a beveled tip 36. The tip 31 on the movable shaft also has a bevelled cut with a pressure relief hole or tunnel 32 to allow tissue or bone fragments to escape. FIGS. 12 and 13 illustrate this type of tip. It is a new safety mechanism. The pressure relief tunnel 32 or hole increases space for additional bone matter collection, and reduces frequency of cleaning significantly, while preventing footplate breakdown from pressure. FIGS. 14 and 15 illustrate a modified version of the tip where the tip 140 is upright and has a cup 142. The tip 144 of the movable shaft has a shape to fit into the cup 142. There is provided a "multibite" chamber that further increases space for larger volume specimen collection. This decreases the amount of time and effort required to perform the procedure. FIGS. 16–17 illustrate a jaws and scoop tip for removing a larger amount of tissue. The tip 150 on the movable shaft 155 is pivotally secured to the stationary shaft 165. The tip 160 of the stationary shaft forms the lower half of the scoop.

Figure 25:
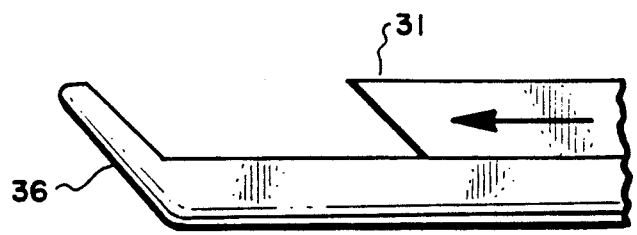
FIG. 25 illustrates the side view of a modified arc tip rongeur cutting against pedicle.
Figure 26:
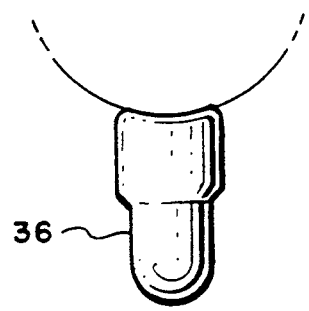
FIG. 26 illustrates the end elevational view of the tip illustrated in FIG. 25.

FIG. 25 illustrates the side view of a modified arc tip rongeur cutting against pedicle. FIG. 26 illustrates the end elevational view of the tip illustrated in FIG. 25.

Figure 27:
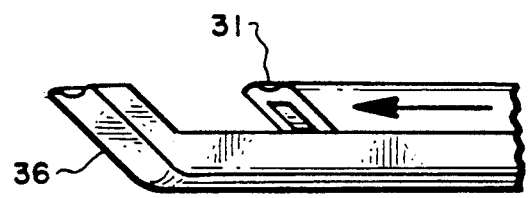
FIG. 27 illustrates a side elevational view of a modified arc tip of a 90 degree or 40 degree angled rongeur with a concave radius cutting edge for fitting against a pedicle bone.

FIG. 27 illustrates a side elevational view of a modified arc tip of a 90 degree or 40 degree angled rongeur with a concave radius cutting edge for fitting against a pedicle bone.

Figure 20:
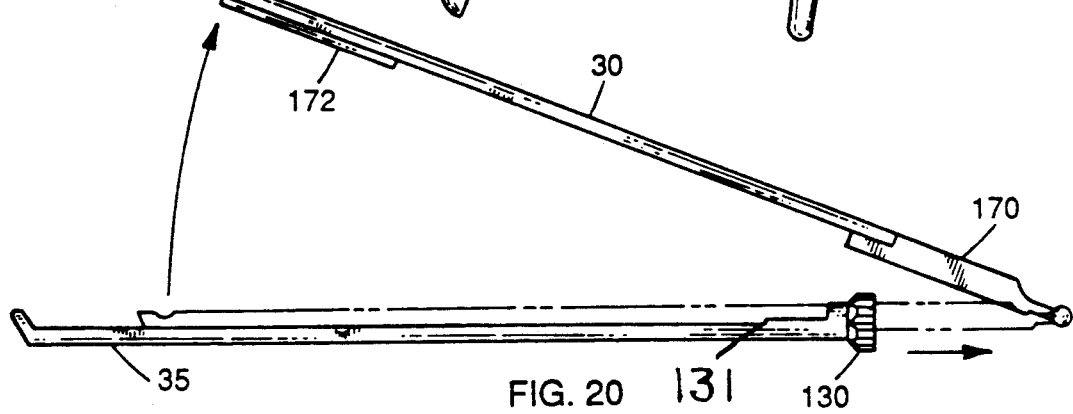
FIG. 20 illustrates how the stationary and movable shafts can be separated from each other.
Figures 21, 22:
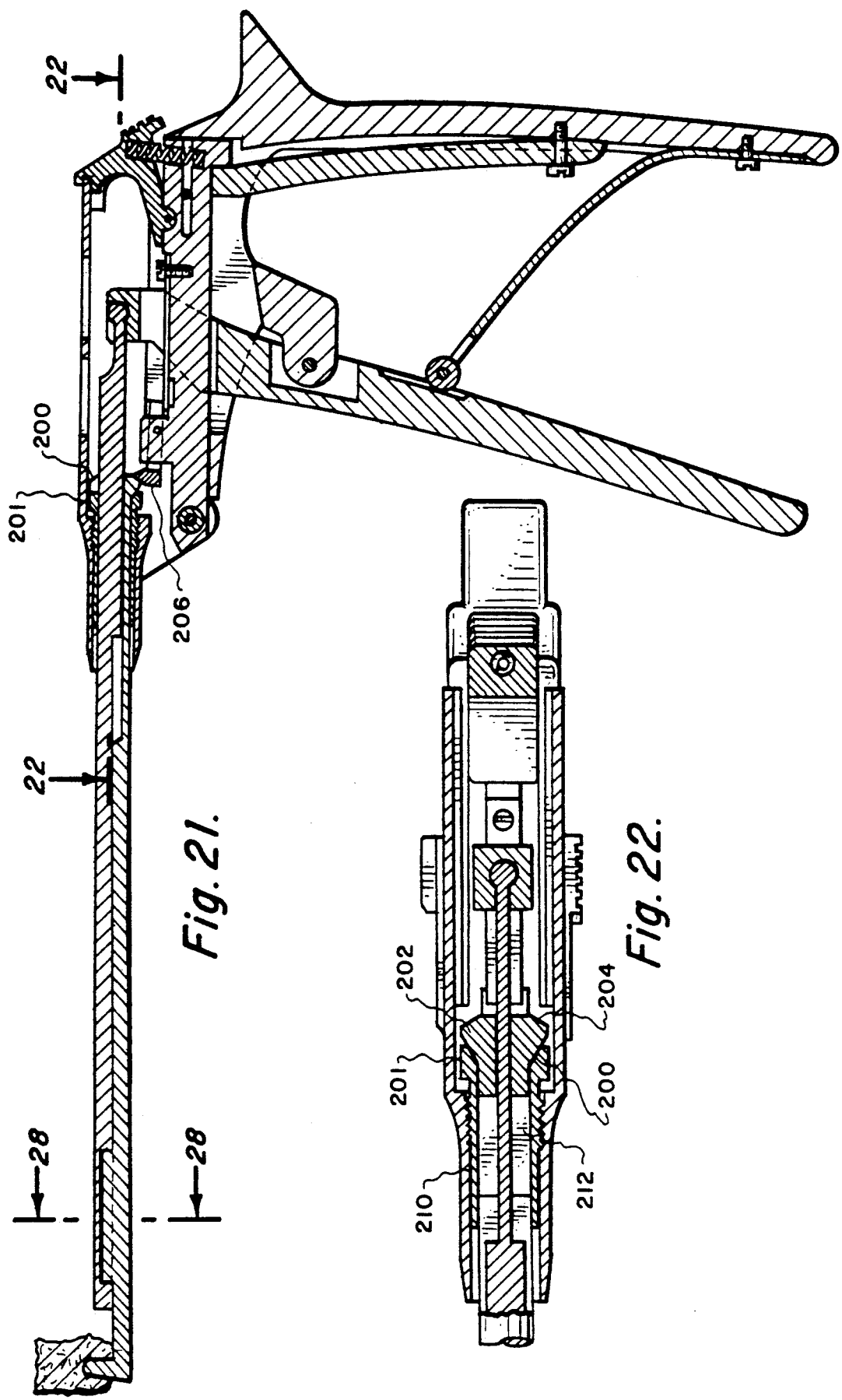
FIG. 21 is similar to FIG. 4 and illustrates the frusto-conical proximal end of the stationary shaft and the wedge-shaped locking member.
FIG. 22 is a longitudinal section taken along the line 22—22 of FIG. 21 and illustrating the interior components of the present invention with the frusto-conical proximal end of the stationary shaft.
Figure 23:
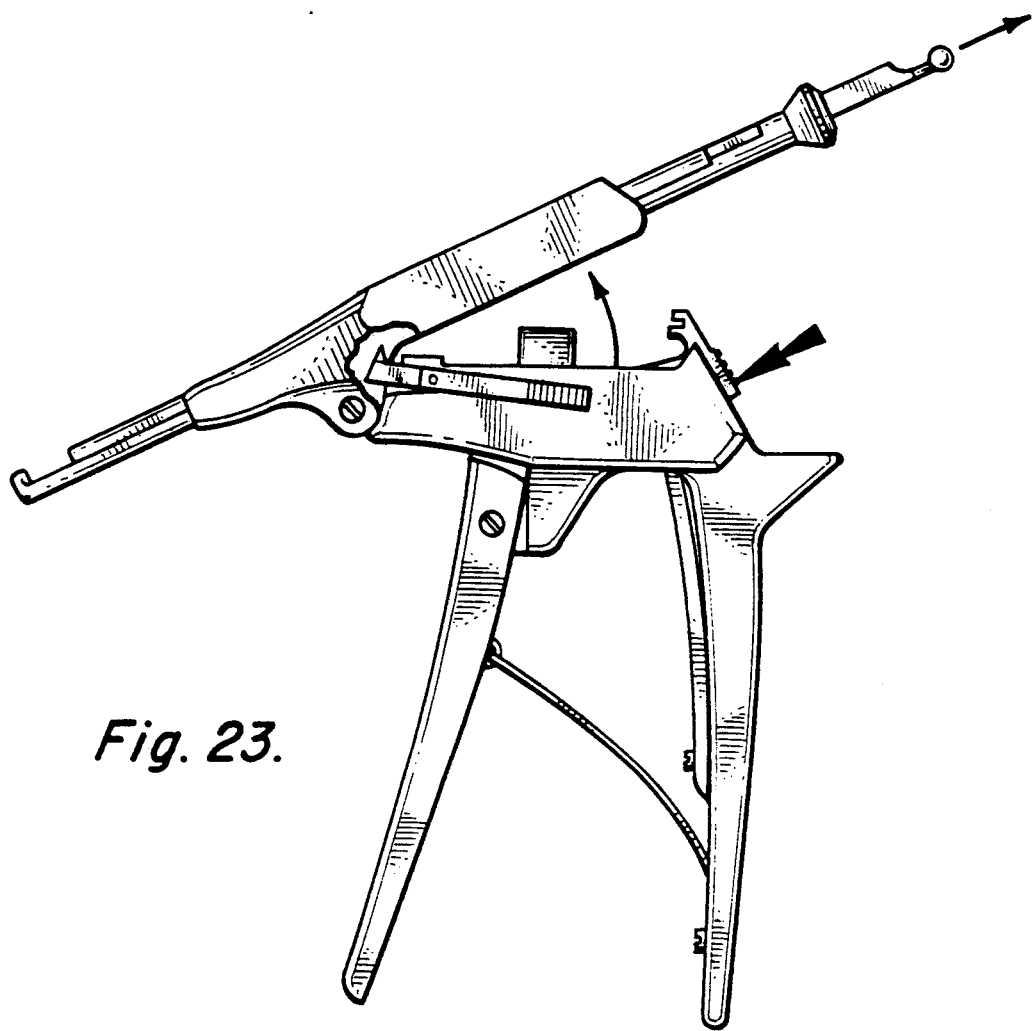
FIG. 23 illustrates how the barrel is cocked open by depressing the trigger and how easily the stationary and movable pair of shafts can be quickly removed from the barrel and reinserted into the barrel, after separating and cleaning both shafts.
Figure 24:
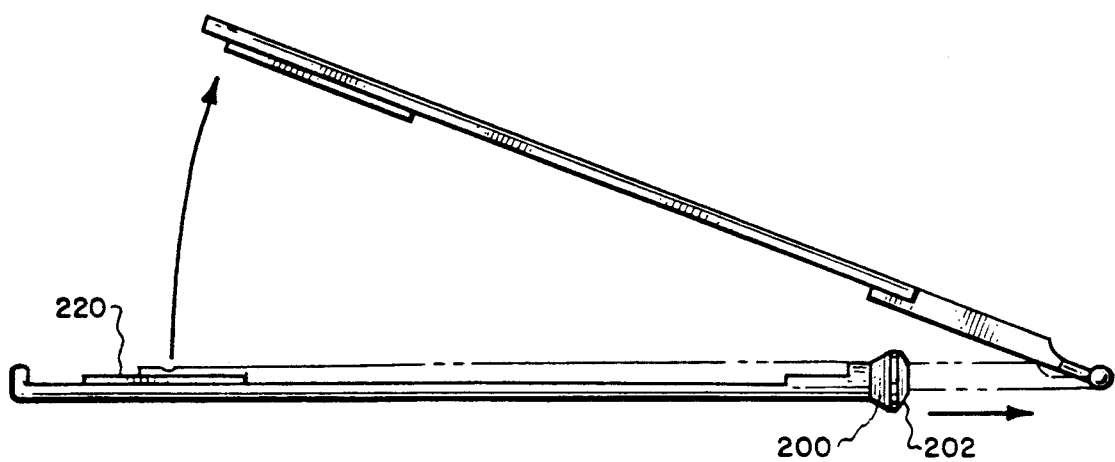
FIG. 24 illustrates how the stationary and movable shafts can be separated from each other.

The shafts 30 and 35 will now be discussed in greater detail. Both are clearly illustrated in FIG. 20. The movable shaft 30, which is longitudinally reciprocable on top of the stationary shaft 35, also has a hemicylindrical shape at its proximal portion as shown in FIG. 8. Both shafts then taper to an oval-shaped cross-section at their distal ends, as illustrated in FIG. 7. There is a 10 degree negative angle for improved view of the operative site in general and micro surgeries. The shaft design delivers the comfort of a more natural wrist and elbow position. The movable shaft has a rectangular end-piece 170 terminating at its proximal end with a small knob or ball 90. The distal end has a tongue portion 172 extending about 2 inches from the end. The tongue portion 172 mates up with a groove portion 174 cut into the flat top surface of the stationary shaft 35 so that the tongue and the groove form a dovetail joint in cross section as illustrated in FIG. 7 to form an interlocking track to prevent the distal end of the movable shaft from disengaging from the stationary shaft end when the instrument is in use. The joint also keeps the tips in alignment. The proximal end of the movable shaft where the rectangular portion 170 is located slides back and forth and reciprocates in a rectangular-shaped groove 176 cut along the longitudinal axis of the stationary shaft towards its proximal end. The star gear has a radial groove to receive and hold the rectangular portion 170. The shafts can be fabricated from metal or plastic.

The barrel 25 is integral with and extends from the chamber cover 27. The barrel 25 is hollowed out and has a cylindrical bore for allowing the two-piece shaft to be inserted into the barrel. The shafts then extend partially from the barrel 25. The cylindrical bore which holds the proximal portion of the shaft is circular in cross section. It also forms a conical flare 26 as the inside chamber of the cover constricts towards the bore. The proximal end of the stationary shaft that has the star gear 130 attached to it slips into this flaring portion 26 in the barrel so that it will only extend a certain portion and then it will stop. The star gear 130 positioned in the conical tapered portion results in a secure fit of the proximal end of the stationary shaft in the barrel. For all practical purposes, the stationary portion of the shaft stays stationary relative to the barrel 25 when the instrument is used. By squeezing the movable handle, the top end 122 of the handle, which mates with the ball end 90 of the movable shaft 30 will push against the movable shaft 30 and force the movable shaft 30 towards and away from the opening of the barrel 25. This slight movement causes the distal tip 31 of the movable shaft to close toward the distal tip 36 of the stationary shaft, closing the bite or jaw area to remove a piece of bone or tissue caught in the bite or jaw area. The stationary shaft 35 and star gear 130 combination allows the surgeon extensive flexibility by allowing him to rotate the shaft about its axis in 45 degree increments either clockwise or counterclockwise to change the angular orientation of the footplate at the distal ends of the shafts. The orientation of the tip of the shaft can be changed by pressing down on either quick release side lever 65, which will disengage the lock 66 on the star gear 130 and shaft to rotate as a unit. This is clearly illustrated in FIGS. 10 and 11. This allows the surgeon to change the orientation of the cutting tips without opening up the barrel and cover part. By simply pressing the lever 65, the shaft combination can be rotated clockwise or counterclockwise in 45 degree increments, or a quarter of a turn per increment to change the angular orientation of the bite.

Figure 19:
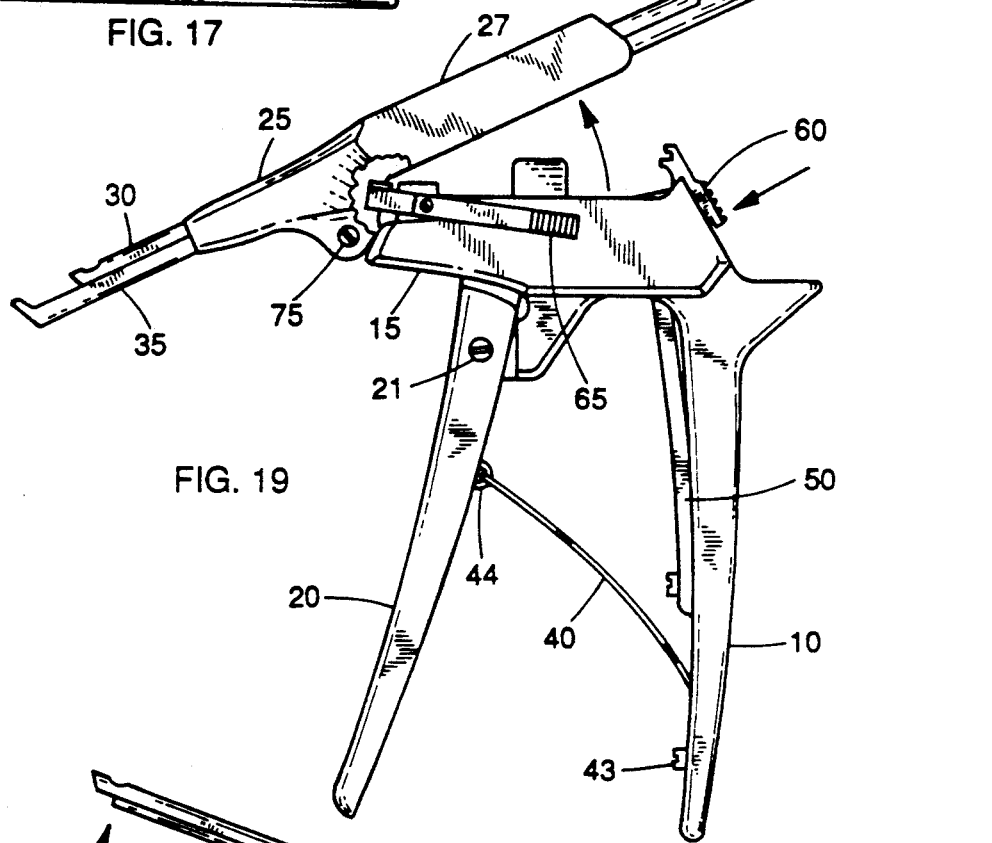
FIG. 19 illustrates how the barrel is cocked open by depressing the trigger and how easily the stationary and movable pair of shafts can be quickly removed from the barrel and reinserted into the barrel, after separating and cleaning both shafts.

Another feature of the shaft is that the two-piece shaft unit can be quickly and easily removed from the instrument, taken apart, cleaned, sterilized, put back together and reinserted in the instrument. A different shaft unit could also be substituted if desired. A disposable biopsy shaft could be used. The shaft is removed by first depressing the trigger 60 at the back of the frame so that the barrel 26 can be cocked open by tilting the combination shaft downwardly relative to its fulcrum point where its attached to the front portion of the carriage 70. By cocking open the barrel, the combination shaft can be forced back out the barrel and the exposed proximal end pulled out through the cover. This is clearly illustrated in FIG. 19. The shaft combination can only be removed this way because the star gear or wheel 130 prevents the shaft from exiting out the front of the bore of the barrel.

There is a small flat spring 68, which has one end screwed to the top of the carriage 70. The free end of the flat spring presses against the locking means 66, which in turn prevents the star gear 130 from freely rotating. The locking means is mounted on the top of the carriage and is pivotally secured between a pair of supports 69. The distal end of the lock contains a pointed tooth 64 which mates with the V-shaped depressions 131 in the star gear 130 to prevent the star gear from rotating unless the tension from the flat spring 68 is relieved. The tension relief is accomplished by pressing one of the quick release levers 65 located on either side of the frame. The lever 65 allows the star gear 130 and the combination shaft 30-35 to be rotated to the angular orientation selected by the surgeon.

Figure 28:
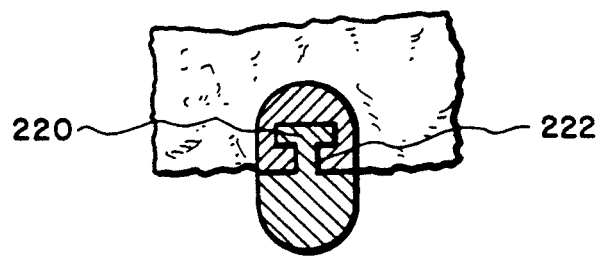
FIG. 28 illustrates a transverse sectional view taken along the line 28—28 in FIG. 21 illustrating the T-shaped tongue and groove joint for keeping the movable and stationary shaft in alignment.

In an alternate, the star gear is replaced with a frustoconical section 200. The alternate is clearly illustrated in FIGS. 21-24. The round proximal head 202 is beveled 204 radially around its circumference. The locking member has a wedge-shaped tooth 206 that frictionally engages against a portion of the beveled edge 204 and acts as a brake to prevent the combination shaft from rotating while in use. The tooth 206 also forces the frusto-conical portion into the bushing to also assist in securing the combination shaft in the barrel and preventing it from rotating while in use. The tooth 206 could have several modifications. The only requirement is that the tooth 206 acts as a brake and a stop against the frusto-conical section. There is also a cylindrical threaded hollow bushing 210 screwed in the bore of the barrel. The hollow bore 212 of the bushing 210 is funnel-shaped for receiving and holding the proximal end of the combination shaft. The bushing has a ring 201 at its proximal end. The surface of the frusto-conical section of the stationary shaft fits securely in the funnel portion of the bushing bore 212. The two surfaces also assist in preventing the combination shaft from rotating, and the bushing 210 aligns and securely holds the combination shaft in place while the instrument is in use. The bushing has a pair of slots at its distal end (not shown). This allows for a tool to be inserted in the barrel to tighten down the bushing in the barrel. A metal glue, such as Locktite is initially applied to the threads of the bushing before the bushing is threaded into the bore of the barrel. The Locktite also prevents the bushing from loosening in the barrel. The combination shaft with the frusto-conical proximal end has the slip joint modified to a T-shaped tongue 220 extending upwardly from the stationary shaft, and the complementary T-shaped groove 222 in the movable shaft. This is clearly illustrated in FIG. 28. This alternate still allows the surgeon to adjust the angular orientation of the cutting tip. It allows for a smaller adjustment. The star gear allows only 45 degree angular adjustment in steps. The frusto-conical portion allows adjustment as little as one degree. There is no requirement that the adjustment be in steps.

The various tips shown in the drawings allow versatility in the operation of the rongeur. The surgeon does not require a separate rongeur for each tip. There could be a series of different tips available as a combination shaft. The surgeon can simply cock open the cover, remove one combination shaft having a particular cutting tip, and replace it with another combination shaft. Also, the barrel with the bushing can be used with the star gear combination shaft if necessary. The only requirement is that the star gear be of the same dimensions as the funnel-shaped bore in the bushing. The wedge-shaped tooth 206 can lock the star gear in place.

The back area of the carriage 70 contains an open horizontal positioning groove 180 cut into the end and there is a transverse pin 182 positioned between the frame and through the groove in the carriage so the carriage can only move a limited amount within its channel. The bottom of the trigger 60 is also secured to the top of the carriage and there is a coil spring 59 in a groove extending vertically adjacent the top of the stationary handle 10. The spring presses against the trigger to keep the trigger in the locked position. The only way to release the trigger is to press down on the knurled portion of the trigger to release the trigger which is pivotally secured to the top of the carriage thereby allowing the barrel and cover to be tilted open to gain access to the inside chamber and for removal of the shaft.

While the present invention has been shown and described herein in what is conceived to be the best mode contemplated, it is recognized that departures may be made therefrom within the scope of the invention which is therefore not to be limited to the details disclosed herein but is to be afforded the full scope of the invention.

What is claimed is:

1. A rongeur surgical instrument comprising:
   a frame having a front portion, a midsection, a rear portion, and a channel;
   a carriage having a slot means and slidably engaged in said channel of said frame;
   means on said carriage for engaging a tensioning means;
   barrel means secured to said carriage for receiving a shaft means;
   a stationary handle integral with an extending below said rear portion of said frame;
   arm means and slot means located at said midsection of said frame;
   a movable handle pivotally secured to said arm means and having its proximal end extending up and through said slot means on said frame on said slot means on said carriage;
   tensioning means having one end secured to said stationary handle and said other end positioned adjacent said engagement means on said carriage for maintaining said carriage stationary in said channel of said frame unless excessive force is applied by the surgeon gripping said handles whereby said tensioning means allows said carriage to move to prevent damage to the instrument;
   shaft means extending from said barrel for removing a portion of bone or tissue.

2. The rongeur instrument as recited in claim 1 wherein said shaft means comprises a stationary shaft and a movable shaft slidably engageable with each other.

3. The instrument as recited in claim 2 further comprising:
   cutting means at the end of said shaft combination for removing a portion of bone or tissue.

4. The device as recited in claim 1 wherein said tensioning means comprises:
   post means and spring means positioned between said carriage and said stationary handle.

5. A rongeur surgical instrument comprising:
   a frame having a front portion, a midsection, a rear portion, and a channel;

a carriage having a slot means and slidably engaged in said channel of said frame;

means on said carriage for engaging a tensioning means;

barrel means secured to said carriage for receiving a shaft means;

a stationary handle integral with and extending below said rear portion of said frame;

arm means and slot means located at said midsection of said frame;

a movable handle pivotally secured to said arm means and having its proximal end extending up and through said slot means on said frame and said slot means on said carriage;

tensioning means having one end secured to said stationary handle and said other end positioned adjacent said engagement means on said carriage for maintaining said carriage stationary in said channel of said frame unless excessive force is applied by the surgeon gripping said handles whereby said tensioning means allows said carriage to move to prevent damage to the instrument;

shaft means extending from said barrel for removing a portion of bone or tissue;

locking means mounted on said carriage means for preventing said shaft combination from rotating about its axis;

quick release means for releasing said locking means mounted on said carriage to allow the surgeon to quickly rotate said shaft means to adjust the angle of the tip at the distal end of said shaft means.

6. The device as recited in claim 5 wherein:

said locking means includes a frusto-conical section on said shaft;

bushing having a funnel-shaped bore and mounted in said barrel means for receiving said frusto-conical section on said shaft.

7. A rongeur surgical instrument comprising:

a frame having a front portion, a midsection, a rear portion, and a channel;

a stationary handle integral with and extending below said rear portion of said frame;

arm means and slot means in said midsection of said frame; carriage means having a front portion, a midsection and a rear portion slidably secured in said channel of said frame;

slot means in said midsection of said carriage means;

a movable handle pivotally secured to said front portion of said frame at said arm means and having its proximal end extending up and through said slot of said frame;

a transverse shoulder extending from below said rear portion of said carriage means;

stiff spring means having one end secured to said frame and said other end abutting against said transverse shoulder of said carriage means;

integral barrel and cover means pivotally secured to said front portion of said carriage means;

two-piece shaft means extending from said barrel for removing a portion of bone or tissue;

said two-piece shaft means includes a stationary shaft and a moveable shaft;

a star gear secured to said proximal end of said stationary shaft;

locking means mounted on said carriage means for preventing said shaft combination from rotating about its axis;

quick release means for releasing said locking means mounted on said carriage to allow the surgeon to quickly rotate the shaft combination to adjust the angle of the tip at the distal end of said shaft combination.

8. A rongeur surgical instrument comprising:

a frame having a front portion, a midsection, a rear portion, and a channel;

a stationary handle integral with and extending below said rear portion of said frame;

arm means and slot means in said midsection of said frame;

a movable handle pivotally secured to said front portion of said frame at said arm means and having its proximal end extending up and through said slot of said frame;

carriage means having a front portion, a midsection and a rear portion slidably secured in said channel of said frame;

integral barrel and cover means pivotally secured to said front portion of said carriage means;

a two-piece shaft means extending from said barrel for removing a portion of bone or tissue:

said two-piece shaft means includes a stationary shaft and a movable shaft;

a star wheel secured to said proximal end of said stationary shaft;

locking means mounted on said carriage means for preventing said shaft combination from rotating about its axis;

quick release means for releasing said locking means mounted on said carriage to allow the surgeon to quickly rotate the shaft combination to adjust the angle of the tip at the distal end of said shaft combination;

locking and release means mounted on said frame for holding said barrel and cover means in place while in use, and for allowing said barrel and cover means to be cocked open to allow said shaft combination to be removed from said instrument for quick replacement or for cleaning.

9. A rongeur surgical instrument comprising:

a frame having a front portion, a midsection, a rear portion, and a channel;

a stationary handle integral with and extending below said rear portion of said frame;

arm means and slot means in said midsection of said frame;

a movable handle pivotally secured to said arm means and having its proximal end extending up and through said slot of said frame;

carriage means having a front portion, a midsection and a rear portion slidably secured in said channel of said frame;

integral barrel and cover means pivotally secured to said front portion of said carriage means;

shaft means extending from said barrel for removing a portion of bone or tissue;

release means mounted on said frame for allowing said barrel and cover means to be cocked open to allow said shaft means to be removed from said instrument for quick replacement or for cleaning.

* * * * *